United States Patent [19]

Chupp et al.

[11] Patent Number: 4,908,057

[45] Date of Patent: Mar. 13, 1990

[54] SUBSTITUTED 2,6-SUBSTITUTED 1,2- OR 1,6-DIHYDRO PYRIDINE COMPOUNDS

[75] Inventors: John P. Chupp, Kirkwood; Len F. Lee, St. Charles; William F. Goure, Maryland Heights; John M. Molyneaux, Creve Coeur, all of Mo.

[73] Assignee: Monsanto Company, St. Louis, Mo.

[21] Appl. No.: 227,030

[22] Filed: Aug. 1, 1988

[51] Int. Cl.$^4$ .................... C07D 401/06; A01N 43/40
[52] U.S. Cl. ............................................ 71/92; 71/94; 546/279; 546/278; 546/281
[58] Field of Search ...................... 546/278, 279, 281; 71/94, 92

[56] References Cited

U.S. PATENT DOCUMENTS

| | | | |
|---|---|---|---|
| 4,493,729 | 1/1985 | Hirtzbach | 546/316 |
| 4,556,414 | 12/1985 | Ambrosi et al. | 546/270 |
| 4,607,041 | 8/1986 | Baxter et al. | 546/193 |
| 4,698,093 | 10/1987 | Lee et al. | 546/193 |
| 4,826,532 | 5/1989 | Sing et al. | 546/275 |

*Primary Examiner*—Jane T. Fan
*Attorney, Agent, or Firm*—James C. Bolding

[57] ABSTRACT

Disclosed herein are dihydropyridine dicarboxylic acid amide derivatives which are useful as herbicides, and herbicidal compositions and methods using same.

21 Claims, No Drawings

SUBSTITUTED 2,6-SUBSTITUTED 1,2- OR 1,6-DIHYDRO PYRIDINE COMPOUNDS

This invention relates to a new class of 2,6-substituted 1,2- or 1,6-dihydro pyridinecarboxylic acid derivatives having a wide range of activity as herbicides.

Pyridine and dihydropyridine derivatives have, for many years, been investigated for use in the biological sciences. For example, 2,6-bis-(trifluoromethyl)-4-pyridinols have been found useful as herbicides and fungicides as disclosed in U.S. Pat. No. 3,748,334. Such compounds are characterized by substitution in the 4-position by a hydroxy radical. In addition to the hydroxy radical, the pyridine nucleus may also be substituted with bromo, chloro or iodo radicals. Trifluoromethyl pyridine derivatives have also been disclosed in U.S. Pat. Nos. 2,516,402 and 3,705,170 wherein the nucleus is further substituted by halogens as well as numerous other substituents. Some of these compounds are also noted to be useful as herbicides.

Also known because of their fungicidal activity are 4-substituted 2,6-dichloro-3,5-dicyanopyridines wherein the 4-position is substituted with alkyl, phenyl, naphthyl or pyridyl groups. Such compounds are disclosed in U.S. Pat. No. 3,284,293, while similar compounds are disclosed in U.S. Pat. No. 3,629,270 wherein the 4-position is substituted with a heterocyclic group wherein the hetero atom is oxygen or sulfur.

Pyridine dicarboxylate compounds useful as herbicides are described in U.S. Pat. No. 4,682,184. These compounds have fluorinated methyl groups at the 2- and 6-positions and carboxylic acid derivative at the 3- and 5-positions.

Other pyridine dicarboxylate compounds including pyrazole amides are disclosed in U.S. Pat. No. 4,698,093. 1,4- and 3,4-dihydropyridine dicarboxylate herbicides are described in Great Britain Patent 2,145,085.

BRIEF DESCRIPTION OF THE INVENTION

It is an object of this invention to provide herbicidal methods and compositions utilizing the novel 1,2- and 1,6-dihydropyridines of this invention.

The novel compounds of this invention useful as herbicides are represented by the generic formula

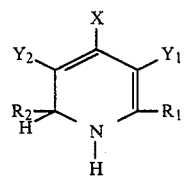

wherein:
one of $Y_1$ and $Y_2$ is

in which $Z_1$ is selected from

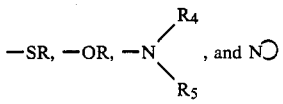

where R, $R_4$ and $R_5$ are the same or different and are selected from lower alkyl, lower alkenyl, lower alkynyl, haloalkyl, haloalkenyl, and cyanoalkyl, and

is selected from azetidinyl and a saturated or unsaturated 5-membered heterocyclic ring moiety containing 1-2 nitrogen atoms, the remaining atoms being carbon atoms, optionally substituted with 1 to 3 groups which are the same or different and are selected from lower alkyl, lower alkoxy, cyano, halo, nitro, haloalkyl, alkoxyalkyl, and dialkoxyalkyl; $Z_2$ is selected from O and S; and $R_4$ and $R_5$ are selected from hydrogen and lower alkyl;
the other of $Y_1$ and $Y_2$ is

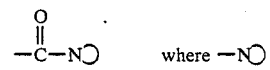

is as defined above;
$R_1$ and $R_2$ are independently selected from fluorinated methyl, chlorofluorinated methyl, chlorinated methyl, and lower alkyl radicals, provided that one of $R_1$ and $R_2$ must be a fluorinated methyl or chlorofluorinated methyl radical;
X is selected from lower alkyl, cycloalkylalkyl, alkoxyalkyl, and alkylthioalkylcyclobutyl.

The term "lower alkyl" means herein both straight and branched chain radicals having 1 to 7 carbon atoms which include, but are not limited to, ethyl, methyl, n-propyl, 1-ethylpropyl, 1-methylpropyl, n-butyl, 2,2-dimethylpropyl, pentyl, isobutyl, isopropyl.

The terms "lower alkenyl" and "lower alkynyl" herein mean alkenyl and alkynyl groups having 3 to 7 carbon atoms. Examples of such alkenyl groups include 2-propenyl, 2-butenyl, 3-butenyl, 2-methyl-2-propenyl and the like. Examples of such lower alkynyl groups include 2-propynyl, and so forth.

The term "haloalkyl" is intended to mean alkyl radicals substituted with one or more halogen atoms.
The term

as used herein includes azetidinyl as well as radicals derived from pyrazole, pyrrole, pyrrolidine, dihydropyrazole and pyrazolidine, with or without the substituents named above.

The term "fluorinated methyl" means herein methyl radicals having one or more fluorine atoms attached thereto including radicals wherein all hydrogen atoms are replaced by fluorine.

The term "chlorofluorinated methyl" means herein a methyl radical having at least one hydrogen replaced by fluorine and at least one other hydrogen replaced by chlorine.

DETAILED DESCRIPTION OF THE INVENTION

The compounds of this invention are readily prepared by reaction of a heterocyclic amine with the desired pyridinecarboxylic acid halide or pyridinedicarboxylic acid halide in the presence of a base (which may be an excess of the heterocyclic amine), followed by reduction of the pyridine ring on the nitrogen atom and an adjacent carbon atom using sodium borohydride to form the 1,2- or 1,6-dihydropyridine compound. Steps 1–9 which follow set out in detail the preparation of three specific acid halides which are used as starting materials for the compounds of this invention. Other acid halides may be readily prepared using the procedures of Steps 1–9 by varying the ketoester and aldehyde used in Step 1 to obtain the desired substituents in the pyridinedicarboxylate product as shown in U.S. Pat. No. 4,692,184, the disclosure of which is specifically incorporated herein by reference. Other suitable pyridinedicarboxylate acid halides as starting materials are shown in U.S. Pat. No. 4,692,184 in Examples 44–51 and 82–83 inclusive. Other acid halide starting mterials may be readily prepared using the techniques set out in that U.S. Patent.

The following Steps 1–9 illustrate an example of the procedures for preparation of the acid halide compounds which are the starting materials for making the amides of the present invention. In these steps, a β-ketoester is reacted with an aldehyde to form a pyran (Step 1). The pyran is then reacted with ammonia to form a dihydroxypiperidine (Step 2), which is dehydrated to make a dihydropyridine compound (Step 3). The dihydropyridine is then oxidized or dehydrofluorinated to prepare a pyridinedicarboxylate compound (Step 4).

The ester groups of the pyridinedicarboxylate compound are the ester groups of the β-ketoester, and the 4-position of the pyridine is substituted with the same substituent as is on the aldehyde reagent.

When the pyridinedicarboxylate is substituted at the 2- or 6-position with a trifluoromethyl radical and at the other of these positions with a difluoromethyl radical, hydrolysis of the pyridine dicarboxylate compound occurs selectively on the side having the $CF_2H$ group when one equivalent of a base such as KOH is employed in the hydrolysis (Step 8). When two equivalents of base or more are employed, the dicarboxylate is hydrolyzed to the diacid (Step 5). The diacid may be converted to the diacid chloride by treatment with a chlorinating agent such as $SOCl_2$ or $PCl_5$. Following this conversion, treatment with one equivalent of an alcohol selectively esterifies the diacid chloride on the chloride group adjacent the $CF_2H$ group.

Step 10 below illustrates the reaction of a heterocyclic amine, in tis instance pyrazole, with an acid chloride to form a pyridine carboxamide which is the immediate precursor of a compound of this invention.

STEP 1

Preparation of dimethyl 2,6-bis(trifluoromethyl)-2,6-dihydroxy-4-isobutyl-tetrahydro-3,5-pyrandicarboxylate To a mechanically stirred mixture of 280 g (2.0 mole) of 80% pure methyl trifluoroacetoacetate and 86 g (1.0 mole) of isovaleraldehyde is added 1 ml of piperidine. An exothermic reaction occurs and the temperature of the reaction mixture reaches 105° C. After 5 hours of stirring, the reaction mixture is triturated with 450 ml of hexane and 30 ml of ether and cooled with a dry ice bath to give 1.68 g of a first crop, m.p. 83°–87° C. and 14.51 g of a second crop, m.p. 67°–73° C.

The first crop is the desired product which contains a mixture of 5:1 cis and trans isomers.

Anal. Calc'd for $C_{15}H_{20}F_6O_7$: C, 42.26; H, 4.73. Found: C, 42.54; H, 4.77.

The second crop is a 2:1 mixture of cis and trans isomers. The mother liquor is concentrated to give 344 g of a residue which is a crude mixture of cis and trans isomer of the desired product.

STEP 2

Preparation of dimethyl 2,6-bis(trifluoromethyl)-2,6-dihydroxy-4-isobutyl-3,5-piperidinedicarboxylate To a solution of 344 g (0.920 mole) crude product from Step 1 in 500 ml of tetrahydrofuran (THF) is passed 58 g (3.41 mole) of gaseous ammonia for 3 hours. The reaction mixture is concentrated and the residue (332 g) is recrystallized from hexane-ether to give 53.7 g (13% yield from methyl trifluoroacetoacetate) of the desired product as a white solid, m.p. 102°–106° C.

Anal. Calc'd for $C_{15}H_{21}F_6N_1O_6$: C, 42.36; H, 5.00; N, 3.29. Found: C, 42,84; H, 4.94; N, 3.29.

The mother liquor is concentrated to provide more of the crude desired product.

STEP 3

Preparation of a 2:1 mixture of dimethyl 2,6-bis(trifluoromethyl)-1,4-dihydro-4-isobutyl-3,5-pyridinedicarboxylate and its 3,4-dihydropyridine isomer To an ice water cooled mixture of 200 ml of concentrated sulfuric acid and 200 ml of methylene chloride is added 48.7 g (0.115 mole) of the product of Step 2 at once. The reaction mixture is stirred for 20 minutes and poured into 1 L. of ice water. The methylene chloride layer is separated and washed once with 100 ml of saturated sodium bicarbonate, dried and concentrated to give 28.0 g (64.6%) of crude product. A portion (5.0 g) of this product is kugelrohr distilled at 0.5 torr (pot temperature at 120° C.) to give 4.8 of the desired product, $n_D^{25}$ 1.4391.

Anal. Calc'd for $C_{15}H_{17}F_6N_1O_4$: C, 46.28; H, 4.40; N, 3.60. Found: C, 46.39; H, 4.44; N, 3.60.

Step 3 product may be prepared in better overall yield without isolation of Step 1 and Step 2 product by the following procedure To a mechanically stirred mixture of 340.3 g (1.98 mol) of 98.9% pure methyl trifluoroacetoacetate (MTFAA), 100 mL of toluene and 0.86 g (0.01 mol) of piperidine was added 90.5 g (1.03 mol) of isovaleraldehyde in 20 minutes. The reaction was exothermic causing a rise of temperature to 83° C. The reaction mixture was maintained at 80° C. for 3 hours. $^{19}$F NMR showed that the reaction was 89% complete. Heat was removed, and the reaction mixture was diluted with 125 mL of toluene and stirred overnight (16 hours). Gaseous ammonia was passed through the reaction mixture, the exotherm caused a rise of temperature to 68° C. in 50 minutes. A water cooling bath was applied to the reaction vessel to reduce the reaction temperature to 53° C. while ammonia was passed continuously. A total of 47.3 g (2.78 mol) of ammonia was passed in 1.5 hours. The reaction mixture was diluted with 100 mL of toluene. A Claisen distillation head was attached to the reaction vessel.

Excess ammonia and parts of toluene were removed in vacuo (water aspirator) while temperature was maintained at 26° C. An additional 200 mL of toluene was added, and the distillation was continued to remove a total of 200 mL of distillate in 1.5 hours. The reation mixture was diluted with 100 mL of toluene and cooled to 5° C. with an ice bath. Sulfuric acid (453 g, 4.53 mol) was added in 5 minutes. The exotherm caused the temperature to rise to 25° C. The temperature gradually subsided to 5° C. in 10 minutes and was maintained at 5° C. for 40 minutes. An additional 95 g (0.95 mol) of sulfuric acid was added, and the reaction mixture was stirred at 5° C. for 20 minutes before being poured into a mixture of 500 mL of toluene and 2 L of ice water. The toluene layer was separated and the aqueous layer was extracted once with 500 mL of toluene. The combined toluene extracts were washed successively with 500 mL of water, 500 mL of saturated aqueous NaHCO$_3$, 500 mL of brine and concentrated in vacuo to 363.6 g of an oil. GC area percent analysis indicated that the oil contained 9% of 3,4-dihydropyridine isomer and 75.4% of 1,4-dihydropyridine isomer corresponding to and overall yield of 82.9% from MTFAA.

STEP 4

Preparation of dimethyl 2-(difluromethyl)-6-(trifluoromethyl)-4-isobutyl-3,5 pyridine dicarboxylate (a) Reaction of the Product of Step 3 with DBU A mixture of 23.0 g (0.0591 mole) of the product of Step 3, 12.2 g (0.077 mole, of 96% pure DBU, and 100 ml of THF is held at reflux for 3 days and poured into 250 ml of 3N HCl. The oil precipitate is extracted into ether (2×100 ml). The ether extracts are dried (MgSO$_4$) and concentrated to give 14.4 g of an oil which, according to $^1$H NMR, contained the desired product and acidic products. This oil is dissolved in ether and extracted with 100 ml of saturated sodium bicarbonate. The ether layer is dried (MgSO$_4$) and concentrated to give 8.9 g of an oil which is 71% pure desired product (by $^{19}$F NMR).

The sodium bicarbonate extract is acidified with concentrated HCl to give an oil which is extracted into ether. The ether layer is dried (MgSO$_4$) and concentrated to give 4.8 g of a residue which contained monocarboxylic acid and dicarboxylic acid (9:1) derived from the desired product. This residue is treated with 3.0 g (0.0217 mole) of potassium carbonate, 20 ml of methyl iodide, and 50 ml of acetone. The mixture is held at reflux for 42 hours and concentrated. The residue is treated with water and extracted with ether (2×100 ml). The ether layer is dried and concentrated. The residue is kugelrohr distilled at 1 torr (pot temperature of 130° C.) to give 5.1 g (23.4% from Step 3) of the desired product as an oil, $n_D^{25}$ 1.4478. This product crystallizes after standing, m.p. 36°–37° C.

Anal. Calc'd for $C_{15}H_{16}F_5N_1O_4$: C, 48.79; H, 4.37; N, 3.79. Found: C, 48.75; H, 4.39; N, 3.77.

The 71% pure desired product described previously was chromatographed by HPLC using 3% ethyl acetate/cyclohexane as eluent to give an earlier fraction (0.79 g, retention time 7–8.5 minutes) which was identified as methyl 6-(difluoromethyl)-4-(isobutyl)-2-(trifluoromethyl)-3-pyridinecarboxylate. The second fraction (retention time 8.5–18.5 minutes) is an additional 6.4 g (29.4%) of pure desired product, $n_D^{25}$ 1.4474.

(b) Reaction of the Product of Step 3 with Tributylamine

A mixture of 38.9 g of an 80% pure product of Step 3 and 20.5 g of tributylamine is heated to 155° C. in 30 minutes. The reaction mixture was cooled to 30° C. and diluted with 100 ml of toluene. The toluene solution is washed successively with 6N hydrochloric acid, saturated sodium bicarbonate, and brine, dried and concentrated to give 36.4 g of a 73% pure product which corresponds to an 86% yield. This reaction can also be carried out in excess of tributylamine (10 equivalent) giving essentially similar results.

(c) Reaction of the Product of Step 3 with Tributylamine in Toluene

A mixture of 38.9 g of an 80% pure product of Step 3, 20.4 g of tributylamine and 30 ml of toluene is heated to 115° C. in 40 minutes and held at 115° C. for 1 hour and 40 minutes. The reaction mixture is cooled and worked up as in (b) above to give 36.3 g of a 76% pure product which correspnds to a 90% yield.

(d) Reaction of the Product of Step 3 with Triethylamine

A mixture of 11.8 g of an 80% pure product of Step 3 and 3.34 g of triethylamine is heated at 100° C. for 10 minutes, then at 125° C. for 10 minutes. The reaction mixture was cooled and worked up as in (b) above to give 8.14 g of a 76% pure product which corresponds to a 63% yield.

(e) Reaction of the Product of Step 3 with 2,6-Lutidine in the Presence of a Catalytic Amount of DBU A mixture of 5.0 g of product of Step 3 and 2.13 g of 2,6-lutidine is heated at 143° C. for 30 minutes. Two drops of DBU are added and the reaction mixture is heated for additional 1 hour and 30 minutes, cooled and worked up as in (b) above to give 4.23 g of the desired product. The reaction can also be carried out in excess of 2,6-lutidine and catalytic amount of DBU without solvent or in the presence of toluene as solvent giving similar results.

STEP 5

Preparation of 2-(difluoromethyl)-6-(trifluoromethyl)-4-isobutyl-3,5-pyridinedicarboxylic acid A 5-liter flask was charged with 894 g (2.42 mol) of the compound of Step 4 and 1 liter of water. To this was added a solution of 574 g (8.7 mol) of KOH in 800 ml of water. The mixture was refluxed overnight, after which HPLC showed that the reaction was complete. The flask was cooled to room temperature, acidified with HCl, and stirred until the organic phase solidified. The solids were filtered, washed with water, and dried in a fluid bed dryer. The diacid was obtained (756 g, 91.6% yield) as a brown solid.

STEP 6

Preparation of 3,5-bis-(chlorocarbonyl)-2-(difluoromethyl)-4-isobutyl-6-(trifluoromethyl)pyridine The diacid product of Step 5 (37.06 g, 0.108 mole) was refluxed with 150 ml $SOCl_2$ for three hours. At this time, $^{19}F$ NMR indicated the reaction was complete. The excess $SOCl_2$ was removed by rotary evaporation, leaving a dark oil which was the bis-acid chloride. This was Kugelrohr distilled at 100° C. to give a colorless oil.

STEP 7

Preparation of methyl 5-chlorocarbonyl-2-(difluoromethyl)-4-isobutyl-6-(trifluoromethyl)pyridine-3-carboxylate The product of Step 6 was then dissolved in 100 ml THF followed by 100 ml methanol. After 2½ hours the solvent was evaporated, leaving 31.2 g of white solid, m.p. 71°-75° C. in 77% yield.

STEP 8

Preparation of 2-(difluoromethyl)-4-isobutyl-6-(trifluoromethyl)-3,5-pyridinedicarboxylic acid, 5-methyl ester A 1-liter 4-necked flask was charged with 300 gm of product of Step 4 and about 200 ml ethanol. In a separate flask was combined 59.14 g (0.896 mol) of 85% KOH and about 100 ml of water. The aqueous solution was poured into the organics and the flask was equipped with a mechanical stirrer, thermometer, nitrogen inlet and a water cooled consenser. The reaction mixture was heated to reflux, refluxed for 45 minutes and was cooled. The reaction mixture was concentrated and the concentrate was diluted with water and extracted once with ethyl ether. The ether extract (to remove starting material) was discarded. The aqueous solution was acidified with concentrated HCl and the orange precipitate that resulted was extracted with ethyl ether. The aqueous solution was extracted with ether 3 times. The ether extracts were combined and dried over anhydrous magnesium sulfate, filtered and concentrated to yield 253.13 g (87.5% yield) of the monoacid ester.

STEP 9

Preparation of methyl 2-(difluoromethyl)-3-chlorocarbonyl-4-isobutyl-6-(trifluoromethyl)-5-pyridinecarboxylate The acid (253 g 0.7121 mol) from Step 8 was refluxed for 24 hours in approximately 250-300 ml of thionyl chloride. The reaction mixture was concentrated to yield 244.59 g of acid chloride in 91.9% yield. $n_D^{25}$ 1.4614.

STEP 10

3-Pyridinecarboxylic acid, 2-(difluoromethyl)-4-(2-methylpropyl)-5-[(1H-pyrazol-1-yl)carbonyl]-6-(trifluoromethyl), methyl ester Methyl 5-(chlorocarbonyl)-2-(difluoromethyl)-4-(2-methylpropyl)-6-(trifluoromethyl)-3-pyridinecarboxylate (2.09 g, 0.0056 mole), 50 ml $CH_2Cl_2$ and 0.88 g (0.013 mole) of pyrazole were combined at ice bath temperature. After 1 hour there was no reaction. The $CH_2Cl_2$ was evaporated and replaced by 30 ml $CCl_4$. An additional 0.35 g of pyrazole was added. This mixture was refluxed overnight. $^{19}F$ NMR showed ~10% starting material and the remainder product. The reaction mixture was washed with $H_2O$ and extracted with $CH_2Cl_2$. The $CH_2Cl_2$ layer was dried with $MgSO_4$, filtered and concentrated to a nearly colorless oil. This was purified by chromatography in 40% $CH_2Cl_2$/cyclohexane to give 1.9 g colorless oil, which gradually solidified, m.p. 49°-52° C., 87% yield.

In compounds of the invention where the $Z_1$ group is SR, a thiol is substituted for the alcohol for reaction with the acid chloride. Where the $Z_1$ group is $$-N\bigcirc$$

one of the 5-membered heterocyclic amines is employed for reaction with the acid chloride.

As stated above, compounds of this invention are prepared from the corresponding pyridine compound by reduction with sodium borohydride ($NaBH_4$) usually in a suitable solvent such as DMF. The temperature at which the reduction is carried out is not critical; room temperature up to about 100° C. is a suitable practical temperature range.

Preparation of compounds of this invention will become clear by reference to the following examples.

As used throughout the specification, including the following Examples, the following abbreviations have the following meanings:

| | |
|---|---|
| DMF | Dimethyl formamide |
| EtOAc | Ethyl acetate |
| Aqueous acidic workup | The crude DMF reaction solution is diluted with an equal volume of diethyl ether and poured onto a 3:1 (v:v, total volume ca. 1 l) of ice cold dilute HCl and diethyl ether. The ether phase is separated and the aqueous phase is washed once with 500 ml of diethyl ether. The ether phases are combined, dried ($MgSO_4$), and concentrated to afford the crude product as a yellow-orange oil or solid. |

EXAMPLES 1 AND 2

3-Pyridinecarboxylic acid, 2-(difluoromethyl)-1,2-dihydro-4-(2-methylpropyl)-5-(1H-pyrazol-1-ylcarbonyl)-6-(trifluoromethyl)-, methyl ester (Example 1); and 3-pyridinecarboxylic acid, 2-(difluoromethyl)-1,6-dihydro-4-(2-methylpropyl)-5-(1H-pyrazol-1-ylcarbonyl)-6-(trifluoromethyl), methyl ester (Example 2)

To a solution of 16.0 g (0.040 mol) of 3-Pyridinecarboxylic acid, 2-(difluoromethyl)-4-(2-methylpropyl)-5-(1H-pyrazol-1-ylcarbonyl)-6-(trifluoromethyl)-, methyl ester (product of Step 10 above) in 50 ml of DMF was added 1.5 g (0.040 mol) of $NaBH_4$. The mixture was heated to 50° C., and held at 50° C. for 2 hours, then stirred overnight prior to workup. The material was poured into a stirred mixture of ether, ice water and diluted HCl, and the ether layer was dried over $MgSO_4$ then stripped of solvent to give 15.2 g of material. Kugelrohr distillation gave 14.3 g of distillate which after chromatography on silica-gel with 4% EtOAc/ hexanes as eluent afforded 4 g (9.8 mmol, 25% yield) of the first title compound above.

Anal. calc'd for $C_{17}H_{18}F_5N_3O_3$: C, 50.13; H, 4.45; N, 10.32. Found: C, 50.14; H, 4.45; N, 10.25.

A later fraction, which was collected only after switching to 7% EtOAc/hexanes as eluent, gave 1.3 g (3.1 mmol, 8% yield) of the second title compound, which was recrystallized from methylcyclohexane and a slight amount of EtOAc: mp 132°–136° C.

Anal. calc'd. for $C_{17}H_{18}F_5N_3O_3$: C, 50.13; H, 4.45; N, 10.32. Found: C, 49.90; H, 4.55; N, 9.98.

The preparation of additional dihydropyridines of the present invention by the NaBH4 reduction of the corresponding pyridine is typified by the following Examples 3–14.

EXAMPLES 3 AND 4

3-Pyridinecarboxylic acid, 2-(difluoromethyl)-1,6-dihydro-4-(2-methylpropyl)-5-(1H-pyrazol-1-ylcarbonyl)-6-(trifluoromethyl)-, ethyl ester (Example 3) and 3-Pyridinecarboxylic acid, 2-(difluoromethyl)-1,2-dihydro-4-(2-methylpropyl)-5-(1H-pyrazol-1-ylcarbonyl)-6-(trifluoromethyl)-, ethyl ester Reaction of 17.4 g (0.0415 mol) of 3-Pyridinecarboxylic acid, 2-(difluoromethyl)-4-(2-methylpropyl)-5-(1H-pyrazol-1-ylcarbonyl)-6-(trifluoromethyl)-, ethyl ester, 1.93 g (0.0511 mol) of NaBH4 and 100 ml of DMF afforded 16.3 g of crude product after acidic aqueous workup. Chromatography of silica-gel with 15% EtOAc/hexanes elution afforded 2.4 g of crude Example 3 and 4.3 g of crude Example 4. Recrystallization of the former from hexanes afforded 1.77 g (4.2 mmol, 10% yield) of pure compound: mp 134.5°–137° C.

Anal. calc'd. for $C_{18}H_{20}F_5N_3O_3$: C, 51.31; H, 4.78; N, 9.97. Found: C, 51.55; H, 4.81; N, 9.78.

Chromatography of crude Example 4 on silica-gel with 10% EtOAc/hexanes elution followed by recrystallization from hexanes afforded 1.75 g (4.15 mmol, 10% yield) of pure compound: mp 89°–91° C.

Anal. calc'd for $C_{18}H_{20}F_5N_3O_3$: C, 51.31; H, 4.78; N, 9.97. Found: C, 51.45; H, 4.75; N, 9.91.

EXAMPLES 5 AND 6

3-Pyridinecarboxylic acid, 2-(difluoromethyl)-1,2-dihydro-4-(cyclopropylmethyl)-5-(1H-pyrazol-1-ylcarbonyl)-6-(trifluoromethyl)-, methyl ester (example 5) and 3-pyridinecarboxylic acid, 2-(difluoromethyl)-1,6-dihydro-4-(cyclopropylmethyl)-5-(1H-pyrazol-1-ylcarbonyl)-6-(trifluoromethyl)-, methyl ester (Example 6)

Reaction of 15.03 g (0.0373 mol) of 3-Pyridinecarboxylic acid, 2-(difluoromethyl)-4-(cyclopropylmethyl)-5-(1H-pyrazol-1-ylcarbonyl)-6-(trifluoromethyl)-, methyl ester and 1.61 g (0.043 mol) of NaBH4 in 100 ml of DMF afforded 17.5 g of crude product after acidic aqueous workup. Chromatography on silica-gel with 11% EtOAc/hexanes elution afforded two main fractions. Chromatography of the more mobile fraction on silica-gel with 10% EtOAc/hexanes elution followed by recrystallization from hexanes afforded 1.75 g (4.32 mmol, 12% yield) of Example 5: mp 96°–98° C.

Anal. calc'd for $C_{17}H_{16}F_5N_3O_3$: C, 50.38; H, 3.98; N, 10.37. Found: C, 50.44; H, 3.98; N, 10.33.

Chromatography of the less mobile fraction on silica-gel with 16% EtOAc/hexanes elution afforded 2.0 g (4.93 mmol, 13% yield) of Example 6: $n_D^{35}$ 1.5195.

Anal. calc'd. for $C_{17}H_{16}F_5N_3O_3$; C, 50.38; H, 3.98; N, 10.37. Found: C, 50.38; H, 4.16; N, 9.73.

EXAMPLES 7 AND 8

3-Pyridinecarbothioic acid, 2-(difluoromethyl)-1,6-dihydro-4-(2-methylpropyl)-5-(1H-pyrazol-1-ylcarbonyl)-6-(trifluoromethyl)-, S-methyl ester (Example 7) and 3-pyridinecarbothioic acid, 2-(difluoromethyl)-1,2-dihydro-4-(2-methylpropyl)-5-(1H-pyrazol-1-ylcarbonyl)-6-(trifluoromethyl)-, S-methyl-ester (Example 8)

Reaction of 16.0 g (0.038 mol) of 3-Pyridinecarbothioic acid, 2-(difluoromethyl)-4-(2-methylpropyl)-5-(1H-pyrazol-1-ylcarbonyl)-6-(trifluoromethyl)-, S-methyl ester and 1.6 g (0.042 mol) of NaBH4 in 100 ml of DMF afforded, after acidic aqueous workup, 16.8 g of crude products. Chromatography on silica-gel with 10% EtOAc/hexanes elution afforded two main fractions. The more mobile fraction was repurified by chromatography on silica-gel with 7% EtOAc/hexanes elution followed by Kugelrohr distillation (150° C. @ 0.1 Torr) to afford 3.79 g (8.95 mmol, 24% yield) of Example 8; $n_D^{37.5}$ 1.5275.

Anal. calc'd. for $C_{17}H_{18}F_5N_3O_2S_1$: C, 48.23; H, 4.29; N, 9.92. Found: C, 48.75; H, 4.40; N, 9.98.

The less mobile fraction was repurified on silica-gel with 10% EtOAc/hexanes elution followed by Kugelrohr distillation (125° C. @ 0.1 Torr) to afford 2.1 g (4.96 mmol, 13% yield) of Example 7: $n_D^{39.5}$ 1.5283.

Anal. calc'd. for $C_{17}H_{18}F_5N_3O_2S_1$: C, 48.23; H, 4.29; N, 9.92. Found: C, 48.42; H, 4.38; N, 9.28.

EXAMPLE 9

3-Pyridinecarboxylic acid, 2-(difluoromethyl)-1,6-dihydro-4-(2-methylpropyl)-5-(3-methyl-1H-pyrazol-1-ylcarbonyl)-6-(trifluoromethyl)-, methyl ester Reaction of 14.70 g (0.0351 mol) of 3-pyridinecarboxylic acid, 2-(difluoromethyl)-4-(2-methylpropyl)-5-(3-methyl-1H-pyrazol-1-ylcarbonyl)-6-(trifluoromethyl)-, methyl ester and 1.45 g (0.0384 mol) of NaBH4 in 100 ml of DMF afforded 14.7 g of crude product following acidic aqueous workup. Chromatography on silica-gel with 10% EtOAc/hexanes elution followed by recrystallization from acetone/hexanes afforded 2.17 g (5.15 mmol, 15% yield) of Example 9: mp 160°–164° C.

Anal. calc'd. for $C_{18}H_{20}N_3O_3F_5$: C, 51.31; H, 4.78; N, 9.97. Found: C, 51.42; H, 4.83; N, 10.03.

EXAMPLE 10

3-Pyridinecarboxylic acid, 2-(difluoromethyl)-1,2-dihydro-4-(2-methylpropyl)-5-(1H-pyrrol-1-ylcarbonyl)-6-(trifluoromethyl)-, methyl ester Reaction of 12.4 g (0.0307 mol) of 3-Pyridinecarboxylic acid, 2-(difluoromethyl)-4-(2-methylpropyl)-5-(1H-pyrrol-1-ylcarbonyl)-6-(trifluoromethyl)-, methyl ester and 1.23 g (0.033 mol) of NaBH4 in 100 ml of DMF followed by an acidic aqueous workup and chromatography on silica-gel with 10% EtOAc/hexanes elution afforded 5.1 g of crude Example 10. Kugelrohr distillation (120° C. @ 1 Torr) afforded 4.5 g (11.07 mmol, 36% yield) of pure Example 10: $n_D^{33.5}$ 1.5088.

Anal. calc'd. for $C_{18}H_{19}N_2O_3F_5$: C, 53.20; H, 4.71; N, 6.89. Found: C, 53.31; H, 4.75; N, 6.84.

EXAMPLES 11 AND 12

3-Pyridinecarboxylic acid, 2-(trifluoromethyl)-1,2-dihydro-4-(2-methylpropyl)-5-(1H-pyrrol-1-ylcarbonyl)-6-(difluoromethyl)-, methyl ester (Example 11) and 3-Pyridinecarboxylic acid, 2-(trifluoromethyl)-1,6-dihydro-4-(2-methylpropyl)-5-(1H-pyrrol-1-ylcarbonyl)-6-(difluoromethyl)-, methyl ester (Example 12)

Reaction of 5.43 g (0.0134 mol) of 3-Pyridinecarboxylic acid, 2-(trifluoromethyl)-4-(2-methylpropyl)-5-(1H-pyrrol-1-ylcarbonyl)-6-(difluoromethyl)-, methyl ester and 0.5952 g (0.0158 mol) of NaBH$_4$ in 60 ml of DMF afforded 6.1 g of crude products after aqueous workup. Chromatography on silica-gel with 7% EtOAc/hexanes elution afforded 3.6 g of product, and a second chromatography on silica-gel with 7% EtOAc/hexanes elution afforded two fractions. After Kugelrohr distillation (110° C. @ 0.05 Torr), the first fraction was found by NMR spectroscopy to be a 1:1 mixture of 1,2- and 1,6-dihydro isomers (Example 11; 1.66 g, 4.09 mmol, 30% yield): $n_D^{35}$ 1.5057.

Anal. calc'd. for $C_{18}H_{19}F_5N_2O_3$: C, 53.18; H, 4.71; N, 6.89. Found: C, 53.48; H, 4.86; N, 6.92.

The second fraction was Kugelrohr distilled (110° C. @ 0.05 Torr) to afford 1.09 g (2.68 mmol, 20% yield) of product which by NMR spectroscopy was found to be a 12:1 mixture of 1,2- and 1,6-dihydro isomers (Example 12): $n_D^{44.5}$ 1.5081.

Anal. calc'd. for $C_{18}H_{19}F_5N_2O_3$: C, 53.18; H, 4.71; N, 6.89. Found: C, 53.36; H, 4.87; N, 6.84.

EXAMPLE 13

3-Pyridinecarboxylic acid, 2-(difluoromethyl)-1,2-dihydro-4-(2-methylpropyl)-5-(1H-pyrrol-1-ylcarbonyl)-6-(1-methylethyl), methyl ester Reaction of 8.2 g (0.0236 mol) of 3-Pyridinecarboxylic acid, 2-(difluoromethyl)-4-(2-methylpropyl)-5-(1H-pyrrol-1-ylcarbonyl)-6-(1-methylethyl), methyl ester and 1.1361 g (0.030 mol) of NaBH$_4$ in 70 ml of DMF at 70° C. for 8 hrs. afforded 7.8 g of crude product after acidic aqueous workup. Chromatography of this crude material on silica-gel with 9% EtOAc/hexanes eluent afforded 1.2 g of impure product, and further chromatography of this material on silica-gel with 5% EtOAc/hexanes as eluent afforded 0.660 g (1.73 mmol, 7% yield) of Example 13: $n_D^{46.5}$ 1.5386.

Anal. calc'd for $C_{20}H_{26}F_2N_2O_3$: C, 63.14; H, 6.89; N, 7.36. Found: C, 63.01; H, 6.84; N, 7.44.

EXAMPLE 14

3-Pyridinecarboxylic acid, 2-(difluoromethyl)-1,2-dihydro-4-(2-methylpropyl)-5-(3-fluoro-1H-pyrazol-1-ylcarbonyl)-6-(trifluoromethyl)-, methyl ester and 3-Pyridinecarboxylic acid, 2-(difluoromethyl)-1,6-dihydro-4-(2-methylpropyl)-5-(3-fluoro-1H-pyrazol-1-ylcarbonyl)-6-(trifluoromethyl)-, methyl ester (3.3:1 mixture)

Reaction of 5.94 g (0.014 mol) of 3-Pyridinecarboxylic acid, 2-(difluoromethyl)-4-(2-methylpropyl)-5-(3-fluoro-1H-pyrazol-1-ylcarbonyl)-6-(trifluoromethyl)-, methyl ester and 0.5992 g (0.0158 mol) of NaBH$_4$ in 70 ml of DMF afforded 7.0 g of crude product after acidic aqueous workup. Chromatography on silica-gel with 10% EtOAc/hexanes elution followed by Kugelrohr distillation (120° C. @ 0.05 Torr) afforded 3.19 g (7.5 mmol, 53% yield) of Example 14 as a 3.3:1 mixture of 1,2- and 1,6-dihydro isomers: $n_D^{41}$ 1.4937.

Anal. calc'd. for $C_{17}H_{17}F_6N_3O_3$: C, 48.01; H, 4.03; N, 9.88. Found: C, 47.99; H, 4.07; N, 9.87.

EXAMPLE 15

3-pyridinecarboxylic acid, 2-(Difluoromethyl)-1,6-dihydro-4-(2-methylpropyl)-5-(1-pyrrolidinylcarbonyl-6-(trifluoromethyl)-, methyl ester Reaction of 10 g (0.0245 mol) of 3-pyridinecarboxylic acid, 2-(difluoromethyl)-4-(2-methylpropyl)-5-(1-pyrrolidinylcarbonyl)-6-(trifluoromethyl)-, methyl ester and 1.0615 g (0.0281 mol)) NaBH$_4$ in 100 ml of DMF at 65° C. afforded 7.8 g of crude product after acidic aqueous workup. Chromatography of the resultant material on silica-gel with 25% EtOAc/hexanes elution gave 3.2 g of crude product. Recrystallization from methylene chloride/hexanes afforded 0.96 g (2.34 mmol, 9.5% yield) of product as a crystalline solid which by NMR analysis contained 35% methylene chloride as solvate: mp 199°–200° C.

Anal. calc'd. for $C_{18}H_{23}F_5N_2O_3$ containing 35 mol % methylene chloride: C, 50.08; H, 5.43; N, 6.37. Found: C, 50.03; H, 5.44; N 6.38.

PRE-EMERGENT HERBICIDE EXAMPLES

As noted above, compounds of this invention have been found to be effective as herbicides, particularly pre-emergent herbicides. Tables A and B summarize results of tests conducted to determine the pre-emergent herbicidal activity of the compounds of this invention. The herbicidal ratings used in Tables A and B were assigned according to a scale based on the percent inhibition of each plant species. The herbicide rating symbols in Tables A and B are defined as follows:

| % Inhibition | Rating |
|---|---|
| 0–24 | 0 |
| 25–49 | 1 |
| 50–74 | 2 |
| 75–100 | 3 |
| Not planted | — |

Species planted, no data N or a blank

For some compounds of this invention data were originally recorded as percent inhibition (or control) in ten percent increments. Where this system was used, the percentages have been mathematically converted to the above equivalent system using the correlation table above.

PRE-EMERGENT ACTIVITY ON WEEDS

One set of pre-emergent tests was conducted as follows:

Topsoil was placed in a pan and compacted to a depth of 0.95 to 1.27 cm. from the top of the pan. A predetermined number of seeds of each of several monocotyledonous and dicotyledonous annual plant species and/or vegetable propagules of various perennial plant species were placed on top of the soil. The soil required to level fill a pan after seeding or adding vegetative propagules were weighed into another pan. A known amount of the test compound dissolved or suspended in an organic solvent or water and applied in acetone or water as a carrier was thoroughly mixed with this cover soil, and the herbicide/soil mixture was used as a cover layer for the previously prepared pan. In Table A below the amount of active ingredient was equivalent to an application rate of 11.2 kg/ha. After treatment, the pans were moved to a greenhouse bench where they were watered as needed to give adequate moisture for germination and growth.

Approximately 10–14 days (usually 11 days) after planting and treating, the pans were observed and the results recorded.

The plant species usually regarded as weeds which were utilized in one set of pre-emergent activity tests, the data for which are shown in Table A, are identified by letter headings printed diagonally above the columns according to the following legend:

| | |
|---|---|
| CATH—Canada thistle* | RHQG—Quackgrass* |
| COBU—Cocklebur | DOBR—Downy Brome |
| VELE—Velvetleaf | BYGR—Barnyardgrass |
| MOGL—Morningglory | ANBG—Annual Bluegrass |
| COLQ—Common Lambsquarters | INMU—Indian Mustard |
| PESW—Pennsylvania Smartweed | WIBW—Wild Buckwheat |
| YENS—Yellow Nutsedge* | |
| RHJG—Rhizome Johnsongrass* | |
| SEJG—Seedling Johnsongrass | |

*Grown from vegetative propagules

In Table A, the second column is the application rate of the compound being tested in kg/ha.

TABLE A

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 1 | 11.21 | 3 | | | 3 | 3 | 3 | 3 | 3 | | | 3 | 3 | 3 | 3 | 3 |
| 2 | 11.21 | 3 | | | 3 | 3 | 3 | 3 | 3 | | | 3 | 3 | 3 | 3 | 3 |
| 3 | 11.21 | 2 | 3 | 3 | 3 | 3 | 3 | 2 | 3 | 3 | 3 | | | | | |
| 4 | 11.21 | 3 | 3 | 3 | 3 | 3 | 3 | 3 | 3 | 3 | 3 | | | | | |
| 5 | 11.21 | 3 | 3 | 3 | 3 | 3 | 3 | 3 | 3 | 3 | 3 | | | | | |
| 6 | 11.21 | 3 | 3 | 3 | 3 | 3 | 3 | 3 | 3 | 3 | 3 | | | | | |
| 7 | 11.21 | 3 | 3 | 3 | 3 | 3 | 3 | 3 | 3 | 3 | 3 | | | | | |
| 8 | 11.21 | 3 | 3 | 3 | 3 | 3 | 3 | 3 | 3 | 3 | 3 | | | | | |
| 9 | 11.21 | 3 | 3 | 3 | 3 | 3 | 3 | 3 | 3 | 3 | 3 | | | | | |
| 10 | 11.21 | 3 | 3 | 3 | 3 | 3 | 3 | 3 | 3 | 3 | 3 | | | | | |
| 11 | 11.21 | 2 | 3 | 3 | 3 | 3 | 3 | 1 | 3 | 3 | 2 | | | | | |
| 12 | 11.21 | 2 | 3 | 3 | 3 | 3 | 3 | 0 | 3 | 3 | 3 | | | | | |
| 13 | 11.21 | 3 | 3 | 3 | 3 | 3 | 2 | 0 | 3 | 3 | 3 | | | | | |
| 14 | 11.21 | 3 | 3 | 3 | 3 | 3 | 3 | 3 | 3 | 3 | 3 | | | | | |
| 15 | 11.21 | 0 | 3 | 3 | 3 | 3 | 2 | 0 | 3 | 3 | 3 | | | | | |

PRE-EMERGENCE ACTIVITY ON WEEDS AND CROPS

In another set of tests, the pre-emergence activity of compounds of this invention was tested on weeds in the presence of crop plants. In these tests the following procedure was used:

Topsoil was sieved to pass through a ½ inch (1.27 cm) screen. Fertilizer was added to the topsoil in some of the tests, while in testing other compounds the fertilizer was omitted. The mixture was then sterilized by exposure to methyl bromide or by heating.

The topsoil mixture was placed in an aluminum pan and compacted to a depth of about 1.27 cm. from the top of the pan. A predetermined number of seeds of each of several monocotyledonous and dicotyledonous plant species and where noted vegetative propagules of various perennial plant species were placed on top of the soil. The soil required to level fill a pan after seeding or adding vegetative propagules was weighed into another pan. A known amount of the test compound was dissolved or suspended in acetone or a suitable organic solvent as a 1% solution or suspension and applied to the cover soil using a sprayer at the desired rate. The spray was thoroughly mixed with this cover soil, and the herbicide/soil mixture was used as a cover layer for the previously prepared pan. Untreated soil was used as a cover layer for control pans. Alternatively, the pans may be covered with the soil layer and the spray solution uniformly applied to the soil surface. When this latter method was used, the statement "surface application" accompanies the test data. In Table B below the amount of active ingredient applied is shown in the Table. After treatment, the pans were moved to a greenhouse bench. Moisture was supplied to each pan as needed for germination and growth. Growth of each species was observed and corrective measures (greenhouse fumigation, insecticide treatment, and the like) were applied as needed.

Approximately 10–14 days (usually 11 days) after planting and treating, the pans were observed and the results recorded.

The pre-emergence data for weeds in the presence of crop plants is shown in the following Table B. In these tests, the plants are identified according to the following column headings printed diagonally above each column, the second column being the rate of application of the test compound in kg/ha:

| | |
|---|---|
| SOBE—Soybean | VELE—Velvetleaf |
| SUBE—Sugarbeet | DOBR—Downy Brome |
| WHEZ—Wheat | PRMI—Proso Millet |
| RICE—Rice | BYGR—Barnyardgrass |
| GRSO—Grain Sorghum | LACG—Large Crabgrass |
| COBU—Cocklebur | GRFT—Green Foxtail |
| WIBW—Wild Buckwheat | CORN—Corn |
| MOGL—Morningglory | COTZ—Cotton |
| HESE—Hemp Sesbania | RAPE—Oilseed Rape |
| COLQ—Common Lambsquarters | COCW—Common Chickweed |
| PESW—Pennsylvania Smartweed | |

TABLE B

| Ex. No. | Rate kg/ha | Sobe | Cotn | Rape | Cobu | Wbp | Mogi | Hese | Cocw | Vele | Whez | Rice | Grso | Corn | Dobr | Prmi | Byr | Lacg | Grft | Subc | Colq | Pesw |
|---|---|---|---|---|---|---|---|---|---|---|---|---|---|---|---|---|---|---|---|---|---|---|
| 1 | 5.6050 | 90 | | | 90 | 100 | 90 | 100 | | 95 | 100 | 100 | 100 | 95 | 100 | 100 | 100 | 100 | 100 | 100 | 100 | 100 |
| | 1.1210 | 85 | 70 | | 70 | 100 | 80 | 100 | | 95 | 100 | 100 | 100 | 90 | 100 | 100 | 100 | 100 | 100 | 100 | 100 | 100 |
| | 0.5605 | 80 | 40 | | 30 | 100 | 80 | 95 | | 95 | 95 | 100 | 100 | 80 | 100 | 100 | 100 | 100 | 100 | 100 | 100 | 100 |
| | 0.2803 | 75 | 0 | | 15 | 100 | 70 | 95 | | 95 | 100 | 95 | 95 | 70 | 98 | 100 | 95 | 100 | 100 | 95 | 100 | 100 |
| | 0.1401 | 65 | 0 | | 10 | 75 | 55 | 98 | | 90 | 40 | 85 | 80 | 40 | 85 | 100 | 98 | 100 | 100 | 80 | 100 | 95 |
| | 0.0701 | 60 | 0 | | 15 | 10 | 20 | 25 | | 75 | 30 | 80 | 75 | 30 | 80 | 100 | 95 | 100 | 100 | 50 | 100 | 95 |
| | 0.0350 | 20 | 0 | | 15 | 15 | 30 | 55 | | 85 | 15 | 55 | 20 | 20 | 90 | 95 | 80 | 100 | 98 | 35 | 20 | 35 |
| | 0.0175 | 15 | 0 | | 10 | 10 | 25 | 30 | | 60 | 0 | 15 | 10 | 15 | 25 | 60 | 70 | 35 | 85 | 30 | N | 15 |
| | 0.0087 | 15 | 0 | | 0 | 0 | 25 | 10 | | 55 | 0 | 10 | 0 | 0 | 15 | 40 | 20 | 90 | 85 | | N | 15 |
| | 0.0044 | 0 | 0 | | 0 | 0 | 0 | 15 | | 20 | 0 | 0 | 0 | 0 | 0 | 0 | 0 | 100 | 100 | | 25 | |
| 2 | 5.6050 | 95 | | | 75 | 100 | 90 | 100 | | 90 | 100 | 100 | 100 | 95 | 100 | 100 | 100 | 100 | 100 | 100 | 100 | 100 |
| | 1.1210 | 90 | 70 | 98 | 25 | 80 | N | 90 | | 90 | 100 | 100 | 100 | 50 | 100 | 100 | 100 | 100 | 100 | 95 | 100 | 100 |
| | 0.5605 | 90 | 40 | 90 | 35 | 100 | 85 | 95 | | 85 | 95 | 100 | 90 | 80 | 90 | 100 | 90 | 100 | 100 | 80 | 100 | 95 |
| | 0.2803 | 85 | 0 | 85 | 0 | 40 | 40 | 85 | | 90 | 90 | 95 | 95 | 40 | 100 | 100 | 95 | 100 | 100 | 50 | | 35 |
| | 0.1401 | 75 | 0 | 85 | 0 | 100 | 75 | 95 | | 90 | 80 | 95 | 90 | 85 | 90 | 100 | 80 | 100 | 100 | 50 | | 30 |
| | 0.0701 | 50 | 0 | 0 | 0 | 40 | 40 | 90 | | 80 | 40 | 90 | 85 | 70 | 0 | 100 | 5 | 100 | 100 | 35 | | 15 |
| | 0.0350 | 25 | 0 | 0 | 25 | 100 | 25 | 70 | | 60 | 10 | 35 | 40 | 15 | 0 | 95 | 100 | 100 | 100 | 35 | 95 | 15 |
| | 0.0175 | 20 | 15 | 0 | 20 | 50 | 20 | 35 | | 0 | 25 | 15 | 25 | 5 | 0 | 35 | 80 | 100 | 100 | | | |
| | 0.0087 | 30 | 90 | | 30 | 85 | 35 | 30 | | 15 | 5 | 50 | 35 | 40 | 100 | 40 | 5 | 95 | 80 | | | |
| | 0.0044 | 0 | 0 | 0 | 0 | 100 | 0 | N | | 0 | 0 | 0 | 20 | 20 | 0 | 0 | 100 | 95 | 100 | | | |
| 3 | 5.6000 | 95 | 95 | 100 | 75 | 100 | 90 | 95 | 100 | 95 | 100 | 100 | 100 | 95 | 100 | 100 | 100 | 100 | 100 | 100 | 100 | 100 |
| | 1.1200 | 100 | 95 | 100 | 0 | 95 | 70 | 85 | 95 | 75 | 100 | 98 | 90 | 95 | 100 | 100 | 100 | 100 | | 100 | 100 | 100 |
| | 0.2800 | 95 | 50 | 95 | 0 | 75 | 25 | 70 | 65 | 60 | 90 | 55 | 90 | 30 | 95 | 90 | 80 | 100 | 85 | 95 | 100 | 95 |
| | 0.0700 | 65 | 35 | 90 | 35 | 35 | 0 | 65 | 0 | 45 | 45 | 0 | 85 | 0 | 45 | 35 | 25 | 95 | 100 | | | |
| | 0.0175 | 0 | 15 | 70 | 0 | 0 | 0 | 0 | 20 | 20 | 45 | NO | 30 | 0 | NO | NO | 0 | 90 | 85 | | | |
| | 0.0087 | 20 | 0 | 20 | 0 | 10 | 0 | 0 | 0 | 0 | 5 | NO | 45 | 20 | NO | NO | NO | 80 | 100 | | | |
| 4 | 5.6000 | 95 | 90 | 100 | 0 | 100 | 90 | 99 | 100 | 100 | 100 | 100 | 100 | 95 | 100 | 100 | 100 | 100 | 100 | 100 | 100 | 100 |
| | 1.1200 | 95 | 70 | 95 | 65 | 100 | 80 | 95 | 100 | 95 | 100 | 100 | 100 | 95 | 100 | 100 | 100 | 100 | 100 | 100 | 100 | 100 |
| | 0.2800 | 80 | 30 | 90 | 0 | 80 | 30 | 95 | 95 | 90 | 95 | 95 | 95 | 55 | 95 | 70 | 100 | 100 | 100 | 95 | 95 | 95 |
| | 0.0700 | 60 | 45 | 45 | 0 | 75 | 0 | 60 | 80 | 65 | 70 | 85 | 75 | 0 | 90 | 75 | 90 | 95 | 90 | 85 | N | 35 |
| | 0.0175 | 30 | 10 | 0 | 0 | 45 | 0 | 20 | 0 | 45 | 55 | 65 | 35 | 0 | 75 | 45 | 90 | 100 | 90 | 50 | 75 | 15 |
| | 0.0087 | 0 | 0 | 0 | 0 | 0 | 0 | 5 | 0 | 20 | 10 | 25 | 25 | 0 | 100 | 0 | 90 | 100 | 100 | 35 | N | 15 |
| 5 | 5.6000 | 98 | 95 | 100 | 75 | 100 | 98 | 100 | 100 | 100 | 100 | 100 | 100 | 100 | 100 | 100 | 100 | 100 | 100 | 100 | 100 | 100 |
| | 1.1200 | 100 | 95 | 100 | 95 | 100 | 85 | 95 | 100 | 100 | 100 | 100 | 100 | 95 | 100 | 100 | 100 | 100 | 100 | 95 | 100 | 95 |
| | 0.2800 | 95 | 50 | 95 | 95 | 100 | 50 | 85 | 100 | 90 | 100 | 95 | 100 | 70 | 100 | 100 | 90 | 100 | 100 | 85 | 95 | 95 |
| | 0.0700 | 90 | 35 | 90 | 35 | 100 | 0 | 25 | 85 | 90 | 90 | 95 | 85 | 70 | 100 | 95 | 95 | 100 | 100 | 50 | N | 90 |
| | 0.0175 | 75 | 0 | 75 | 0 | 65 | 0 | 100 | 60 | 40 | 45 | 65 | 60 | 20 | 75 | 45 | 90 | 95 | 95 | 35 | 75 | 40 |
| | 0.0087 | 40 | 15 | 20 | 0 | 20 | 0 | 25 | 0 | 25 | 25 | 30 | 15 | 0 | 100 | 75 | 90 | 95 | 90 | 35 | N | 50 |
| 6 | 5.6000 | 95 | 90 | 100 | 0 | 100 | 95 | 100 | 100 | 100 | 100 | 100 | 100 | 100 | 100 | 100 | 100 | 100 | 100 | 100 | 100 | 100 |
| | 1.1200 | 95 | 75 | 98 | 75 | 100 | 40 | 95 | 100 | 90 | 95 | 100 | 95 | 95 | 95 | 100 | 100 | 100 | 100 | 100 | 95 | 95 |
| | 0.2800 | 90 | 0 | 95 | 60 | 100 | 0 | 0 | 0 | 85 | 0 | 85 | 60 | 40 | 45 | 45 | 60 | 100 | 100 | 85 | N | 90 |
| | 0.0700 | 60 | 0 | 85 | 10 | 95 | 40 | 95 | 100 | 70 | 95 | 90 | 10 | 25 | 0 | 0 | 100 | 100 | 100 | 50 | 75 | 40 |
| | 0.0175 | 20 | 0 | 75 | 0 | 65 | 30 | 0 | 60 | 35 | 75 | 65 | 60 | 30 | 100 | 100 | 95 | 100 | 95 | 35 | N | 50 |
| | 0.0044 | 0 | 0 | 0 | 0 | 20 | 0 | 0 | 0 | 0 | 0 | 25 | 0 | 0 | 0 | 0 | 0 | 90 | 0 | 20 | 25 | 50 |
| 7 | 5.6000 | 95 | 90 | 95 | 80 | 100 | 80 | 95 | 100 | 95 | 95 | 100 | 100 | 95 | 100 | 100 | 100 | 100 | 100 | 85 | 95 | 90 |
| | 1.1200 | 90 | 70 | 90 | 10 | 100 | 30 | 30 | 90 | 70 | 90 | 90 | 95 | 40 | 75 | 55 | 100 | 100 | 100 | 50 | 75 | 40 |
| | 0.2800 | 30 | 15 | 75 | 0 | 60 | 30 | 30 | 60 | 60 | 30 | 50 | 55 | 25 | 60 | 10 | 90 | 95 | 95 | 35 | N | 50 |
| | 0.0700 | 10 | 10 | 40 | 0 | 20 | 0 | 70 | 60 | 0 | 0 | 40 | 0 | 0 | 0 | 0 | 0 | 90 | 90 | 35 | N | 50 |
| | 0.0175 | 0 | 0 | | 0 | 0 | 0 | 0 | 0 | 0 | 0 | 40 | 0 | 0 | 0 | 10 | 0 | 95 | 75 | 20 | 25 | 50 |

TABLE B-continued

| Ex. No. | Rate kg/ha | Sbe | Cotz | Rape | Cbu | Wbw | Mgl | Hese | Ccw | Vle | Whez | Rice | Grso | Corn | Dobr | Prmi | Bygr | Lacg | Grft | Sube | Colq | Pesw |
|---|---|---|---|---|---|---|---|---|---|---|---|---|---|---|---|---|---|---|---|---|---|---|
| 8 | 0.0087 | 0 | 0 | 0 | 0 | 0 | 0 | 0 | NO | 0 | 0 | 0 | 20 | 10 | 0 | 0 | NO | 95 | 20 | | | |
|  | 5.6000 | 90 | 95 | 100 | 55 | 100 | 90 | 95 | 100 | 90 | 100 | 100 | 100 | 98 | 100 | 100 | 100 | 100 | 100 | | | |
|  | 1.1200 | 75 | 75 | 90 | 0 | 100 | 40 | 90 | 100 | 90 | 100 | 95 | 100 | 90 | 100 | 100 | 100 | 100 | 100 | | | |
|  | 0.2800 | 45 | 20 | 90 | 20 | 95 | 25 | 90 | 100 | 90 | 95 | 95 | 100 | 75 | 95 | 90 | 100 | 100 | 100 | | | |
|  | 0.0700 | 0 | 0 | 45 | 0 | 0 | 0 | 70 | 0 | 40 | 45 | 40 | 50 | 50 | 70 | 90 | 90 | 100 | 95 | | | |
|  | 0.0175 | NO | 15 | 0 | 0 | 0 | 0 | 0 | 0 | 20 | 10 | NO | 35 | 15 | 0 | 25 | 65 | 50 | 40 | | | |
| 9 | 0.0087 | 30 | 20 | 20 | 0 | 0 | 25 | 0 | NO | 0 | 0 | 0 | 0 | 15 | 0 | 0 | 0 | NO | 0 | | | |
|  | 5.6000 | 95 | 60 | 100 | 70 | 100 | 85 | 90 | 100 | 90 | 100 | 100 | 100 | 95 | 100 | 100 | 100 | 100 | 100 | | | |
|  | 1.1200 | 90 | 30 | 90 | 0 | 100 | 70 | 90 | 100 | 90 | 100 | 98 | 100 | 95 | 100 | 100 | 100 | 100 | 100 | | | |
|  | 0.2800 | 25 | 25 | 75 | 0 | 85 | 0 | 75 | 20 | 45 | 55 | 70 | 98 | 40 | 85 | 90 | 85 | 100 | 85 | | | |
|  | 0.0700 | 10 | 10 | 40 | 0 | 55 | 0 | 0 | 0 | 0 | 0 | 35 | 50 | 35 | 0 | 25 | 85 | 30 | 45 | | | |
|  | 0.0175 | 0 | NO | 0 | 0 | 0 | 0 | 0 | 0 | 25 | 0 | NO | 45 | 0 | NO | NO | 0 | NO | 40 | | | |
| 10 | 0.0087 | 0 | 0 | 0 | 0 | 0 | 0 | 0 | 0 | 0 | 0 | 0 | 20 | 0 | 0 | 0 | 0 | 0 | 0 | | | |
|  | 5.6000 | 90 | 90 | 95 | 35 | 100 | 80 | 95 | 100 | 95 | 100 | 100 | 100 | 100 | 100 | 100 | 100 | 100 | 100 | | | |
|  | 1.1200 | 90 | 35 | 95 | 0 | 90 | 55 | 80 | 100 | 80 | 100 | 99 | 100 | 20 | 100 | 100 | 100 | 100 | 100 | | | |
|  | 0.2800 | 25 | 0 | 70 | 0 | 95 | 0 | 20 | 95 | 65 | 90 | 95 | 90 | 25 | 100 | 100 | 80 | 100 | 55 | | | |
|  | 0.0700 | 5 | 0 | 70 | 0 | 0 | 0 | 0 | 35 | 0 | 55 | 55 | 55 | 20 | 70 | 95 | 40 | 80 | 20 | | | |
|  | 0.0175 | 0 | 0 | 0 | 0 | 0 | 0 | 0 | 30 | 20 | 35 | 35 | 25 | 95 | 0 | 35 | 0 | 60 | 25 | | | |
| 11 | 0.0087 | 0 | 0 | 0 | 0 | 0 | 0 | 0 | 0 | 0 | 0 | 0 | 0 | 0 | 0 | 0 | 0 | 0 | 0 | | | |
|  | 5.6000 | 85 | 65 | 90 | 55 | 95 | 65 | 90 | 100 | 90 | 100 | 100 | 100 | 40 | 100 | 100 | 100 | 100 | 100 | | | |
|  | 1.1200 | 0 | 15 | 90 | 0 | 90 | 35 | 70 | 95 | 65 | 95 | 50 | 95 | 40 | 90 | 95 | 95 | 95 | 95 | | | |
|  | 0.2800 | 20 | 0 | 0 | 0 | 0 | 0 | 0 | 0 | 0 | 85 | 20 | 65 | 0 | 70 | 60 | 30 | 35 | 0 | | | |
|  | 0.0700 | 0 | NO | 0 | 0 | 25 | 0 | 0 | 0 | 35 | 0 | 0 | 0 | 0 | 0 | 0 | 0 | 0 | 0 | | | |
|  | 0.0175 | 0 | 10 | 0 | 0 | 0 | 0 | 0 | 0 | 0 | 0 | 0 | 0 | 0 | 0 | 0 | 0 | 0 | 0 | | | |
| 12 | 0.0087 | 0 | 0 | 0 | 0 | 0 | 0 | 0 | 0 | 0 | 0 | 0 | 0 | 0 | 0 | 0 | 0 | 0 | 0 | | | |
|  | 5.6000 | 90 | 70 | 90 | 60 | 100 | 65 | 90 | 100 | 90 | 100 | 100 | 100 | 90 | 100 | 100 | 100 | 100 | 100 | | | |
|  | 1.1200 | 40 | 10 | 80 | 0 | 90 | 0 | 90 | 95 | 70 | 100 | 95 | 95 | 15 | 100 | 100 | 100 | 100 | 90 | | | |
|  | 0.2800 | 40 | 10 | 55 | 5 | 70 | 0 | 0 | 0 | 0 | 70 | 75 | 80 | 0 | 80 | 95 | 95 | 100 | 65 | | | |
|  | 0.0700 | 20 | 15 | 25 | 0 | 35 | 0 | 0 | 0 | 35 | 35 | 30 | 30 | 0 | 30 | 40 | 80 | 100 | 0 | | | |
|  | 0.0175 | 0 | 15 | 0 | 0 | 40 | 0 | 0 | 0 | 0 | 0 | 35 | 0 | 0 | 0 | 0 | 0 | 0 | 0 | | | |
| 13 | 0.0087 | 0 | 0 | 0 | 0 | 0 | 0 | 0 | 0 | 0 | 0 | 0 | 0 | 0 | 0 | 0 | 0 | 0 | 0 | | | |
|  | 5.6000 | 50 | 25 | 90 | 0 | 100 | 35 | 90 | 100 | 100 | 100 | 100 | 100 | 95 | 100 | 100 | 100 | 100 | 100 | | | |
|  | 1.1200 | 30 | 0 | 90 | 5 | 95 | 45 | 45 | 90 | 65 | 85 | 90 | 95 | 25 | 95 | 95 | 55 | 100 | 60 | | | |
|  | 0.2800 | 10 | 0 | 25 | 0 | 30 | 40 | 0 | 0 | 0 | 25 | 10 | 15 | 25 | 50 | 25 | 0 | 30 | 0 | | | |
|  | 0.0700 | 0 | 30 | 0 | 0 | NO | 0 | NO | 0 | NO | 20 | 25 | 0 | 25 | 0 | 0 | 0 | 10 | 0 | | | |
|  | 0.0175 | 0 | 0 | 0 | 0 | 0 | 0 | 0 | 0 | 0 | 0 | 0 | 0 | 0 | 0 | 0 | 0 | NO | 0 | | | |
| 14 | 0.0087 | 0 | 0 | 0 | 0 | 0 | 0 | 0 | 0 | 0 | 0 | 0 | 0 | 0 | 0 | 0 | 0 | 0 | 0 | | | |
|  | 5.6000 | 100 | 90 | 100 | 100 | 100 | 100 | 100 | 100 | 100 | 100 | 100 | 100 | 100 | 100 | 100 | 100 | 100 | 100 | | | |
|  | 1.1200 | 100 | 85 | 100 | 95 | 100 | 95 | 95 | 100 | 95 | 100 | 95 | 100 | 100 | 100 | 100 | 100 | 100 | 100 | | | |
|  | 0.2800 | 95 | 80 | 100 | 90 | 100 | 85 | 70 | 100 | 80 | 95 | 80 | 60 | 60 | 70 | 95 | 90 | 100 | 90 | | | |
|  | 0.0700 | 0 | 10 | 95 | 25 | 60 | 55 | 0 | 40 | 20 | 55 | 25 | 65 | 20 | 50 | 75 | 65 | 100 | 65 | | | |
|  | 0.0175 | 0 | 0 | 60 | 30 | 40 | 0 | 45 | 45 | 0 | 45 | 0 | 99 | 0 | 90 | 100 | 0 | 100 | 0 | | | |
| *15 | 0.0087 | 85 | 65 | 90 | 100 | 100 | 95 | 100 | 100 | 100 | 100 | 100 | 100 | 98 | 100 | 100 | 100 | 100 | 100 | | | |
|  | 5.6000 | 70 | 5 | 95 | 95 | 100 | 80 | 90 | 100 | 95 | 100 | 95 | 95 | 85 | 95 | 95 | 90 | 100 | 90 | | | |
|  | 1.1200 | 45 | 5 | 65 | 90 | 90 | 55 | 20 | 95 | 25 | 85 | 85 | 85 | 50 | 90 | 90 | 95 | 100 | 90 | | | |
|  | 0.2800 | 20 | 25 | 70 | 10 | 65 | 0 | 60 | 55 | 35 | 100 | 35 | 55 | 0 | 65 | 75 | 75 | 99 | 75 | | | |
|  | 0.0700 | 15 | 0 | 0 | 0 | 30 | 0 | 10 | 65 | 0 | 85 | 0 | 40 | 0 | 5 | 30 | 0 | 85 | 10 | | | |

*Inhibition observed at 8 days.

POST-EMERGENCE ACTIVITY ON WEEDS

Topsoil was placed in pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules were covered with soil and leveled. The pans were then placed on a bench in the greenhouse and watered as needed for germination and growth. After the plants reached the desired age (two to three weeks), each pan (except the control pans) was removed to a spraying chamber and sprayed by means of an atomizer. The spray solution or suspension contained about 0.4% by volume of an emulsifying agent and a sufficient amount of the candidate chemical to given an application rate of the active ingredient of 11.2 kg/ha while applying a total amount of solution or suspension equivalent to 1870 L/Ha (200 gallons/acre). The pans were returned to the greenhouse and watered as before and the injury to the plants as compared to those in control pans was observed at approximately 10–14 days (usually 11 days). The plant species used in this set of tests were the same as those used in the first set of pre-emergence tests, and the plant identifying codes are the same as those shown for Table A.

TABLE C

| Ex. No. | Rate kg/ha | Yens | Anbg | Sejg | Dobr | Bygr | Mogl | Cobue | Vele | Inmu | Wibw | Cath | Colqw | Pesw | Rhqg | Rhjg |
|---|---|---|---|---|---|---|---|---|---|---|---|---|---|---|---|---|
| 1 | 11.21 | 0 | | | 0 | 1 | 0 | 0 | 0 | | | 0 | 0 | 0 | 0 | 0 |
| 2 | 11.21 | 0 | | | 0 | 1 | 1 | 1 | 0 | | | 0 | 1 | 0 | 0 | 0 |
| 3 | 11.21 | 0 | 0 | 2 | 0 | 2 | 2 | 2 | 1 | 1 | 1 | | | | | |
| 4 | 11.21 | 0 | 3 | 3 | 2 | 2 | 2 | 1 | 1 | 2 | 2 | | | | | |
| 5 | 11.21 | 0 | 0 | 2 | 1 | 2 | 2 | 2 | 1 | 2 | 2 | | | | | |
| 6 | 11.21 | 0 | 0 | 2 | 0 | 2 | 1 | 1 | 1 | 1 | 2 | | | | | |
| 7 | 11.21 | 0 | 1 | 2 | 0 | 2 | 1 | 1 | 1 | 1 | 2 | | | | | |
| 8 | 11.21 | 0 | 2 | 2 | 0 | 2 | 1 | 1 | 1 | 1 | 1 | | | | | |
| 9 | 11.21 | 0 | 1 | 1 | 0 | 2 | 2 | 1 | 1 | 2 | 2 | | | | | |
| 10 | 11.21 | 0 | 1 | 3 | 0 | 0 | 1 | 1 | 1 | 2 | 1 | | | | | |
| 11 | 11.21 | 0 | 0 | 2 | 0 | 0 | 0 | 0 | 1 | 0 | 0 | | | | | |
| 12 | 11.21 | 0 | 0 | 2 | 0 | 0 | 0 | 0 | 1 | 0 | 0 | | | | | |
| 13 | 11.21 | 0 | 0 | 2 | 0 | 1 | 1 | 1 | 1 | 2 | N | | | | | |
| 14 | 11.21 | 1 | 1 | 3 | 1 | 3 | 1 | 0 | 1 | 1 | 2 | | | | | |
| 15 | 11.21 | 0 | 0 | 0 | 0 | 0 | 2 | 1 | 1 | 2 | 0 | | | | | |

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, and polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring a nonaqueous solution of a water-insoluble active ingredient and an emulsification agent with water until uniform and then homogenizing to give stable emulsion of very finely-divided particles. The resulting concentrated aqueous suspension is characterized by its extremely small particle size, so that when diluted and sprayed, coverage is very uniform. Suitable concentrations of these formulations contain from about 0.1–60% preferably 5–50% by weight of active ingredient, the upper limit being determined by the solubility limit of active ingredient in the solvent.

Concentrates are usually solutions of active ingredients in water-immiscible or partially water-immiscible solvents together with a surface active agent. Suitable solvents for the active ingredient of this invention include dimethylformamide, dimethylsulfoxide, N-methyl-pyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5-60 parts) active ingredient, about 0.25 to 50 parts (preferably 1-25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, uracils, acetic acid or phenol derivatives, thiolcarbamates, triazoles, benzoic acids, nitriles, biphenyl ethers, imidazolinones and the like such as:

HETEROCYCLIC NITROGEN/SULFUR DERIVATIVES

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-α:2',1'-c)-pyrazidiinium salt
5-Bromo-3-isopropyl-6-methyluracil 1,1'-Dimethyl-4,4'-bipyridinium
2-(4-isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate

UREAS

N-(4-chlorophenoxy) phenyl-N,N-dimethylurea
N,N-dimethyl-N'-(3-chloro-4-methylphenyl)urea
3-(3,4-dichlorophenyl)-1,1-dimethylurea
1,3-Dimethyl-3-(2-benzothiazolyl)urea
3-(p-Chlorophenyl)-1,1-dimethylurea
1-Butyl-3-(3,4-dichlorophenyl)-1-methylurea
2-Chloro-N[(4-methoxy-6-methyl-3,5-triazin-2-yl) aminocarbonyl]-benzenesulfonamide
Methyl 2-(((((4,6-dimethyl-2-pyrimidinyl)amino)carbonyl)amino)sulfonyl) benzoate
Ethyl 2-[methyl 2-(((((4,6-dimethyl-2-pyrimidinyl)amino)carbonyl)amino)sulfonyl)] benzoate
Methyl-2((4,6-dimethoxy pyrimidin-2-yl)aminocarbonyl)amino sulfonyl methyl) benzoate
Methyl 2-(((((4-methoxy-6-methyl-1,3,5-triazin-2-yl)amino)carbonyl)amino)sulfonyl) benzoate

CARBAMATES/THIOLCARBAMATES

2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl N,N-diisopropylthiolcarbamate

ACETAMIDES/ACETANILIDES/ANALINES/AMIDES

2-Chloro-N,N-diallylacetamide
N,N-dimethyl-2,2-diphenylacetamide
N-(2,4-dimethyl-5-[[(trifluoromethyl)sulfonyl] amino]phenyl]acetamide N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
α,α,α-Trifluoro-2,6-dinitro-N,N-dipropyl-p-toluidine
N-(1,1-dimethylpropynyl)-3,5-dichlorobenzamide

ACIDS/ESTERS/ALCOHOLS 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol N-(phosphonomethyl) glycine and its salts.
Butyl 2-[4-[(5-trifluoromethyl)-2-pyridinyl)oxy]phenoxy]-propanoate

ETHERS 2,4-Dichlorophenyl-4-nitrophenyl ether
2-Chloro-α,α,α-trifluoro-p-tolyl-3-ethoxy-4-nitrodiphenyl ether
5-(2-chloro-4-trifluoromethylphenoxy)-N-methylsulfonyl 2-nitrobenzamide
1'-(Carboethoxy) ethyl 5-[2-chloro-4-(trifluoromethyl)phenoxy]-2-nitrobenzoate

MISCELLANEOUS 2,6-Dichlorobenzonitrile
Monosodium acid methanearsonate
Disodium methanearsonate
2-(2-chlorophenyl)methyl-4,4-dimethyl-3-isoxazolidinone
7-oxabicyclo (2.2.1) heptane, 1-methyl-4-(1-methyl ethyl)-2-(2-methylphenylmethoxy)-,exo- Fertilizers useful in combination with the active ingredients include, for example ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

I. Emulsifiable Concentrates

| | Weight Percent |
|---|---|
| A. Compound of Example No. 3 | 11.0 |
| Free acid of complex organic phosphate or aromatic or aliphatic hydrophobe base (e.g, GAFAC RE-610, registered trademark of GAF Corp.) | 5.59 |
| Polyoxyethylene/polyoxypropylene block copolymer with butanol (e.g., Tergitol XH, registered trademark of Union Carbide Corp.) | 1.11 |
| Phenol | 5.34 |
| Monochlorobenzene | 76.96 |
| | 100.00 |
| B. Compound of Example No. 14 | |
| Free acid of complex organic phosphate of aromatic or aliphatic hydrophobe base (e.g., GAFAC RE-610) | 5.00 |
| Polyoxyethylene/polyoxypropylene block copolymer with butanol (e.g., Tergitol XH) | 1.60 |
| Phenol | 4.75 |
| Monochlorobenzene | 63.65 |
| | 100.00 |

II. Flowables

| | Weight Percent |
|---|---|
| A. Compound of Example No. 2 | 25.00 |
| Methyl cellulose | 0.3 |
| Silica Aerogel | 1.5 |
| Sodium lignosulfonate | 3.5 |
| Sodium N—methyl-N—oleyl taurate | 2.0 |
| Water | 67.7 |
| | 100.00 |
| B. Compound of Example No. 1 | 45.0 |
| Methyl cellulose | .3 |
| Silica aerogel | 1.5 |
| Sodium lignosulfonate | 3.5 |
| Sodium N—methyl-N—oleyl taurate | 2.0 |
| Water | 47.7 |
| | 100.00 |

III. Wettable Powders

| | Weight Percent |
|---|---|
| A. Compound of Example No. 5 | 25.0 |
| Sodium lignosulfonate | 3.0 |
| Sodium N—methyl-N—oleyl-taurate | 1.0 |
| Amorphous silica (synthetic) | 71.0 |
| | 100.00 |
| B. Compound of Example 7 | 80.00 |
| Sodium dioctyl sulfosuccinate | 1.25 |
| Calcium lignosulfonate | 2.75 |
| Amorphous silica (synthetic) | 16.00 |
| | 100.00 |
| C. Compound of Example No. 6 | 10.0 |
| Sodium lignosulfonate | 3.0 |
| Sodium N—methyl-N—oleyl-taurate | 1.0 |
| Kaolinite clay | 86.0 |
| | 100.00 |

IV. Dusts

| | Weight Percent |
|---|---|
| A. Compound of Example No. 13 | 2.0 |
| Attapulgite | 98.0 |
| | 100.00 |
| B. Compound od Example No. 10 | 60.0 |
| Montmorillonite | 40.0 |
| | 100.00 |
| C. Compound of Example No. 11 | 30.0 |
| Ethylene glycol | 1.0 |
| Bentonite | 69.0 |
| | 100.00 |
| D. Compound of Example No. 13 | 1.0 |
| Diatomaceous earth | 99.0 |
| | 100.00 |

V. Granules

| | Weight Percent |
|---|---|
| A. Compound of Example No. 4 | 15.0 |
| Granular attapulgite (20/40 mesh) | 85.0 |
| | 100.00 |
| B. Compound of Example No. 6 | 30.0 |
| Diatomaceous earth (20/40) | 70.0 |
| | 100.00 |
| C. Compound of Example No. 8 | 1.0 |
| Ethylene glycol | 5.0 |
| Methylene blue | 0.1 |
| Pyrophyllite | 93.9 |
| | 100.00 |
| D. Compound of Example No. 10 | 5.0 |
| Pyrophyllite (20/40) | 95.0 |
| | 100.00 |

When operating in accordance with the present invention, effective amounts of the compounds of this invention are applied to the soil containing the seeds, or vegetative propagules or may be incorporated into the soil media in any convenient fashion. The application of liquid and particulate solid compositions on the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in *Webster's New International Dictionary*, Second Edition, Unabridged (1961). Thus, the term refers to any substance or media in which vegetation may take root and grow, and includes not only earth but also compost, manure, muck, humus, sand, and the like, adapted to support plant growth.

Although the invention is described with respect to specific modifications, the details thereof are not to be construed as limitations. .

What is claimed is:

1. A compound represented by the formula

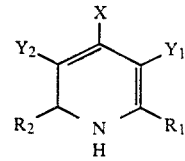

wherein:
one of $Y_1$ and $Y_2$ is

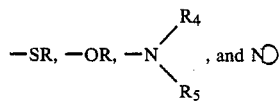

in which $Z_1$ is selected from

, and 

where R, $R_4$ and $R_5$ are the same or different and are selected from lower alkyl, lower alkenyl, lower alkynyl, lower haloalkyl, lower haloalkenyl, and lower cyanoalkyl, and

—N⟨ is selected from azetidinyl and a saturated or unsaturated 5-membered heterocyclic ring moiety containing 1-2 nitrogen atoms, the remaining atoms being carbon atoms, optionally substituted with 1 to 3 groups which are the same or different and are selected from lower alkyl, lower alkoxy, cyano, halo, nitro, lower haloalkyl, lower alkoxy-lower alkyl and lower dialkoxy-lower alkyl; $Z_2$ is selected from O and S;

the other of $Y_1$ and $Y_2$ is $$-\overset{O}{\underset{\|}{C}}-N$$    where —N⟨ is as defined above;

$R_1$ and $R_2$ are independently selected from fluorinated methyl, chlorofluorinated methyl, chlorinated methyl, and lower alkyl radicals, provided that one of $R_1$ and $R_2$ must be a fluorinated methyl or chlorofluorinated methyl radical;

X is selected from lower alkyl, lower (cycloalkyl)-lower alkyl, lower alkoxy-lower alkyl, lower alkylthio-lower alkyl and cyclobutyl.

2. A compound according to claim 1 wherein $Z_2$ is O.

3. A compound according to claim 2 in which $Z_1$ is selected from —SR and —OR and R is lower alkyl.

4. A compound according to claim 3 wherein one of $R_1$ and $R_2$ is —$CF_3$ and the other is $CF_2H$.

5. A compound according to claim 4 in which X is selected from 2-methylpropyl, cyclopropylmethyl and cyclobutyl.

6. A compound according to claim 5 wherein

—N⟨ in the other of $Y_1$ and $Y_2$ is pyrazolyl.

7. A compound according to claim 6 in which R is methyl.

8. A herbicidal composition containing as an active ingredient a compound represented by the formula

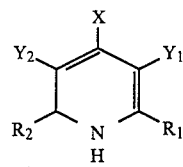

wherein:
one of $Y_1$ and $Y_2$ is

in which $Z_1$ is selected from

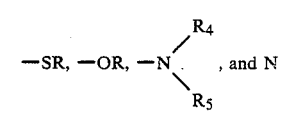

where R, $R_4$ and $R_5$ are the same or different and are selected from lower alkyl, lower alkenyl, lower alkynyl, lower haloalkyl, lower haloalkenyl, and lower cyanoalkyl, and

—N⟨ is selected from azetidinyl and a saturated or unsaturated 5-membered heterocyclic ring moiety containing 1-2 nitrogen atoms, the remaining atoms being carbon atoms, optionally substituted with 1 to 3 groups which are the same or different and are selected from lower akyl, lower alkoxy, cyano, halo, nitro, lower haloalkyl, lower alkoxy-lower alkyl and di(lower alkoxy)-lower alkyl;

the other of $Y_1$ and $Y_2$ is

    where —N⟨ is as defined above;

$R_1$ and $R_2$ are independently selected from fluorinated methyl, chlorofluorinated methyl, chlorinated methyl, and lower alkyl radicals, provided that one of $R_1$ and $R_2$ must be a fluorinated methyl or chlorofluorinated methyl radical;

X is selected from lower alkyl, lower (cycloalkyl)-lower alkyl, lower alkoxy-lower alkyl, lower alkylthio-lower alkyl and cyclobutyl.

9. A composition according to claim 1 wherein $Z_2$ is O.

10. A composition according to claim 2 in which $Z_1$ is selected from —SR and —OR and R is lower alkyl.

11. A composition according to claim 3 wherein one of $R_1$ and $R_2$ is —$CF_3$ and the other is $CF_2H$.

12. A composition according to claim 4 in which X is selected from 2-methylpropyl, cyclopropylmethyl and cyclobutyl.

13. A composition according to claim 5 wherein

in the other of $Y_1$ and $Y_2$ is pyrazolyl.

14. A composition according to claim 6 in which R is methyl.

15. A method for control of undesired vegetation which comprises applying to the plant locus a compound represented by the formula

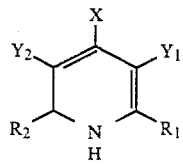

wherein:

one of $Y_1$ and $Y_2$ is

in which $Z_1$ is selected from

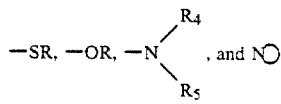

where R, $R_4$ and $R_5$ are the same or different and are selected from lower alkyl, lower alkenyl, lower alkynyl, lower haloalkyl, lower haloalkenyl, and lower cyanoalkyl, and

is selected from azetidinyl and a saturated or unsaturated 5-membered heterocyclic ring moiety containing 1–2 nitrogen atoms, the remaining atoms being carbon atoms, optionally substituted with 1 to 3 groups which are the same or different and are selected from lower alkyl, lower alkoxy, cyano, halo, nitro, lower haloalkyl, lower alkoxy-lower alkyl and di(lower alkoxy)-lower alkyl; Z is selected from O and S;

the other of $Y_1$ and $Y_2$ is

 where —N⌒ is as defined above;

$R_1$ and $R_2$ are independently selected from fluorinated methyl, chlorofluorinated methyl, chlorinated methyl, and lower alkyl radicals, provided that one of $R_1$ and $R_2$ must be a fluorinated methyl or chlorofluorinated methyl radical;

X is selected from lower alkyl, lower alkoxy-lower alkyl, lower alkylthio-lowralkyl and cyclobutyl.

16. A method according to claim 1 wherein $Z_2$ is O.

17. A method according to claim 2 in which $Z_1$ is selected from —SR and —OR and R is lower alkyl.

18. A method according to claim 3 wherein one of $R_1$ and $R_2$ is —$CF_3$ and the other is $CF_2H$.

19. A method according to claim 4 in which X is selected from 2-methylpropyl, cyclopropylmethyl and cyclobutyl.

20. A method according to claim 5 wherein

in the other of $Y_1$ and $Y_2$ is pyrazolyl.

21. A method according to claim 6 in which R is methyl.

* * * * *